United States Patent
Sanchez et al.

(10) Patent No.: US 10,542,930 B1
(45) Date of Patent: Jan. 28, 2020

(54) AUDIO ASSESSMENT FOR ANALYZING SLEEP TRENDS USING MACHINE LEARNING TECHNIQUES

(71) Applicant: BlueOwl, LLC, Bloomington, IL (US)

(72) Inventors: Kenneth Jason Sanchez, San Francisco, CA (US); Vinay Kumar, San Francisco, CA (US)

(73) Assignee: BLUEOWL, LLC, San Francisco, CA (US)

(*) Notice: Subject to any disclaimer, the term of this patent is extended or adjusted under 35 U.S.C. 154(b) by 367 days.

(21) Appl. No.: 15/659,256

(22) Filed: Jul. 25, 2017

(51) Int. Cl.
| | |
|---|---|
| *A61M 21/00* | (2006.01) |
| *A61B 5/00* | (2006.01) |
| *A61B 5/087* | (2006.01) |
| *G06N 20/00* | (2019.01) |

(52) U.S. Cl.
CPC ............ *A61B 5/4815* (2013.01); *A61B 5/087* (2013.01); *A61B 5/4818* (2013.01); *A61B 5/7282* (2013.01); *G06N 20/00* (2019.01); *A61B 5/4809* (2013.01)

(58) Field of Classification Search
CPC .......... A61M 21/00; A61M 2021/0005; A61B 5/4815; A61B 5/4818; G06N 20/00
USPC ...................................................... 600/26–28
See application file for complete search history.

(56) References Cited

U.S. PATENT DOCUMENTS

| | | |
|---|---|---|
| 9,294,732 B2 | 3/2016 | Gillette |
| 9,474,876 B1 | 10/2016 | Kahn et al. |
| 9,600,994 B2 | 3/2017 | Park et al. |
| 9,642,557 B2 | 5/2017 | Gavish et al. |
| 2012/0092171 A1 | 4/2012 | Hwang et al. |
| 2013/0144190 A1 | 6/2013 | Bruce et al. |
| 2014/0051938 A1 | 2/2014 | Goldstein et al. |
| 2014/0051944 A1 | 2/2014 | Gillette |
| 2014/0276167 A1 | 9/2014 | Dasgupta et al. |
| 2015/0009325 A1 | 1/2015 | Kardashov |
| 2015/0342519 A1 | 12/2015 | Zheng |
| 2016/0015315 A1 | 1/2016 | Auphan et al. |
| 2016/0331303 A1 | 11/2016 | Shen et al. |

*Primary Examiner* — John P Lacyk (57) ABSTRACT

A computer system for assessing sound to analyze a user's sleep includes a processor configured to perform operations including: (i) storing sample sound data associated with a plurality of sample sleep events, the sample sound data including a plurality of sample characteristics each respectively associated with at least one sample sleep event of the plurality of sample sleep events; (ii) receiving, from a client device, subject sound data collected during a sleep interval; (iii) analyzing, using a machine learning algorithm, the subject sound data collected during the sleep interval; (iv) identifying, based upon the analyzing, a subject characteristic associated with the subject sound data; (v) comparing the subject characteristic with the plurality of sample characteristics; and (vi) determining, based upon the comparing, whether the subject characteristic substantially matches at least one sample characteristic to identify one or more subject sleep events occurring during the sleep interval.

20 Claims, 5 Drawing Sheets

AUDIO ASSESSMENT FOR ANALYZING SLEEP TRENDS USING MACHINE LEARNING TECHNIQUES

FIELD OF THE INVENTION

The present disclosure relates to systems and methods for audio assessment to analyze sleep trends. More particularly, the present disclosure relates to systems and methods for analyzing a person's sleep patterns using machine learning techniques.

BACKGROUND

Many people experience issues during their sleep, whether due to a diagnosed or diagnosable condition such as sleep apnea or insomnia, or due to unknown conditions or environmental factors, such as sleeping in an area that experiences a lot of noise. However, it can often be difficult to identify a source or cause of poor sleep without undergoing time-consuming, uncomfortable, and/or expensive tests. These tests are often undertaken in a lab rather than in a person's home, which can easily result in the person being unable to sleep comfortably or not exhibiting the same personal or environmental issues with their sleep. In such cases, issues can go unresolved or undiagnosed.

BRIEF SUMMARY

The present embodiments relate to systems and methods for assessing sound data collected during a sleep interval to identify one or more sleep events that occur during that sleep interval. More particularly, the present embodiments relate to using machine learning to compare sound data from the sleep interval to one or more sample sounds. By matching characteristics of the sound data collected during the sleep interval to characteristics of the sample sounds, one or more sleep events occurring during the interval may be identified.

In one aspect, a computer-based method for assessing sound to analyze a user's sleep is provided. The method may be performed using a sound analysis computing device including at least one processor in communication with at least one memory device. The method may include: (i) storing sample sound data associated with a plurality of sample sleep events, the sample sound data including a plurality of sample characteristics each respectively associated with at least one sample sleep event of the plurality of sample sleep events; (ii) receiving, from a client device, subject sound data collected during a sleep interval; (iii) analyzing, using a machine learning algorithm, the subject sound data collected during the sleep interval; (iv) identifying, based upon the analyzing, a subject characteristic associated with the subject sound data; (v) comparing the subject characteristic with the plurality of sample characteristics; and/or (vi) determining, based upon the comparing, whether the subject characteristic substantially matches at least one sample characteristic to identify one or more subject sleep events occurring during the sleep interval. The method may include additional, fewer, and/or alternative steps, including those described elsewhere herein.

In another aspect, a computer system for assessing sound to analyze a user's sleep is described. The computer system includes a processor, and a non-transitory, tangible, computer-readable storage medium having instructions stored thereon that, in response to execution by the processor, cause the processor to perform operations including: (i) storing sample sound data associated with a plurality of sample sleep events, the sample sound data including a plurality of sample characteristics each respectively associated with at least one sample sleep event of the plurality of sample sleep events; (ii) receiving, from a client device, subject sound data collected during a sleep interval; (iii) analyzing, using a machine learning algorithm, the subject sound data collected during the sleep interval; (iv) identifying, based upon the analyzing, a subject characteristic associated with the subject sound data; (v) comparing the subject characteristic with the plurality of sample characteristics; and/or (vi) determining, based upon the comparing, whether the subject characteristic substantially matches at least one sample characteristic to identify one or more subject sleep events occurring during the sleep interval. The computer system may include additional, less, and/or alternative functionality, including that described elsewhere herein.

In yet another aspect, a non-transitory computer readable medium that includes executable instructions for assessing sound to analyze a user's sleep is described. When executed by a sound analysis computing device including at least one processor in communication with at least one memory device, the computer executable instructions may cause the sound analysis computing device to: (i) store sample sound data associated with a plurality of sample sleep events, the sample sound data including a plurality of sample characteristics each respectively associated with at least one sample sleep event of the plurality of sample sleep events; (ii) receive, from a client device, subject sound data collected during a sleep interval; (iii) analyze, using a machine learning algorithm, the subject sound data collected during the sleep interval; (iv) identify, based upon the analysis, a subject characteristic associated with the subject sound data; (v) compare the subject characteristic with the plurality of sample characteristics; and/or (vi) determine, based upon the comparison, whether the subject characteristic substantially matches at least one sample characteristic to identify one or more subject sleep events occurring during the sleep interval. The computer readable medium may include additional, fewer, and/or alternative instructions, including instructions to perform processes described elsewhere herein.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the systems and methods disclosed therein. It should be understood that each Figure depicts an embodiment of a particular aspect of the disclosed systems and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and are instrumentalities shown, wherein.

The Figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION OF THE DRAWINGS

The present embodiments may relate to, inter alia, systems and methods for analyzing a person's sleep patterns using audio assessment and machine learning techniques. In one exemplary embodiment, the process may be performed by at least one front-end system, such as a client device (e.g., a smart phone), and at least one back-end system, such as a web server and/or a database server.

Accordingly, the system may include a client device, such as a personal computer or a mobile communications device. The user may connect to the back-end system via the client device to initiate a process for audio assessment to analyze sleep patterns. More particularly, the backend system may deliver a webpage or a mobile application (e.g., an "app") to the client device. The webpage or app may measure sound data captured during a sleep interval, corresponding generally to an interval of time over which a user is sleeping (or, if a level of sleep quality is low, attempting to get to sleep or remain asleep). In addition, and as described below, the backend system and/or the smartphone app may compare one or more characteristics of sound data collected during the sleep interval ("subject characteristics") to one or more characteristics associated with known sleep events ("sample characteristics") to identify one or more sleep events that occurred during the sleep interval ("subject sleep events"). Such comparison may provide the user insight into one or more sleep conditions or issues the user is experiencing, which may facilitate improving the user's sleep. In addition, the webpage or app may enable the user to enter various user inputs, such as user-identified sleep events, qualitative opinions on sleep quality, and/or other user inputs.

In various embodiments, a backend system (e.g., a web server and/or a database server) and/or a client device may analyze sound data associated with a plurality of known sleep events, also referred to as "sample sleep events." Sleep events may include, for instance, sleep disorders (e.g., sleep apnea, insomnia, sleep movement disorder, snoring, parasomnia, etc.), sleep stages (e.g., falling asleep, light sleep, rapid eye movement (REM) sleep, waking), environmental factors or conditions (e.g., white noise, weather sounds, etc.), and/or other events that may occur during a user's sleep interval. This sample sound data may be stored in a database and may include digital and/or analog sound data associated with the plurality of sample sleep events.

The analysis may be performed based upon one or more machine learning algorithms (as described below), such as one or more machine learning algorithms configured to identify one or more characteristics associated with each of the sample sleep events. The stored sample sound data may include a plurality of sound files associated with respective sample sleep events. In one embodiment, a user associated with training the machine learning algorithm(s), referred to as an "expert user," may indicate the content of each sound file. For instance, the expert user may indicate that one set of sound files contains sample sound data of sleep condition sleep events, such as a person experiencing sleep apnea.

Each of these different sample sleep events may be associated with one or more sound characteristics, such as frequency characteristics, amplitude characteristics, various other waveform characteristics, duration characteristics, and the like. The sample characteristics may be identified by the system (e.g., by training and/or implementing one or more machine learning algorithms) or may be identified by an expert user to the system (e.g., during a training phase for the machine learning algorithm). For example, the expert user may identify one or more characteristics of a sleep apnea sleep event (i.e., the sound(s) made during a sleep apnea sleep event). Additionally or alternatively, the expert user may indicate the content of a sound file of the sample sleep event, and the system may "self-learn" one or more characteristics associated with that sample sleep event. Thus, the system may identify, based upon an analysis of various sound data associated with one or more sleep events, one or more characteristics, such as at least a first "sample characteristic," associated with one or more sample sleep events. Where a particular sample sleep event is associated with a plurality of sample characteristics, these sample characteristics may collectively be referred to as a unique sample sound "signature" or sample sleep event signature. It should be readily understood that certain sample characteristics may be common to a plurality of the sample sleep events (e.g., particular breathing patterns or levels), but that sample sound signatures include a particular set of characteristics that uniquely identify that sample sleep event.

During or after the sleep interval, the system may, in addition, receive, from the client device (which may be disposed or located within a threshold distance from the user during the sleep interval), sound data, such as ambient sound data, collected by the client device within a user's sleeping area (e.g., within a user's bedroom). More particularly, a smartphone app, as described above, running on the client device may "listen" to or detect the sound within the sleeping area. The client device may, in addition (and as described above) include an analog to digital converter, which may convert analog sound data collected by the client device to digital sound data. This sound data collected during the sleep interval may be referred to herein as "subject sound data," to be compared to sample sound data associated with the sample sleep events, as described above.

In response to receiving the subject sound data from the client device, the system may analyze the subject sound data. More particularly, the system may analyze the subject sound data collected during the sleep interval to identify one or more characteristics, such as at least a first "subject characteristic," of the sound data collected during the sleep interval. These subject characteristics may include frequency characteristics, amplitude characteristics, various other waveform characteristics, and the like, associated with the user's sleep during the sleep interval. Further, where a plurality of subject characteristics are identified in conjunction with the subject sound data, the sound characteristics may collectively define a subject sound signature.

In addition, in some cases, the system may identify a plurality of groups of characteristics or a plurality of sound signatures within the subject sound data, such that subject sound data collected during the sleep interval actually includes a plurality of sound signatures. This may occur, for example, as a result of a plurality of distinct sleep events occurring during the sleep interval, such as a first sleep event associated with disrupted sleep and a second sleep event associated with a thunderstorm. Certain sounds may, in other words, intermingle or intermix with one or more other sounds during the sleep interval. The system may, under such a circumstance, identify characteristics associated with both sounds, such that the thunderstorm during the sleep interval is associated with a first subject characteristic, a first group of subject characteristics, or a first subject sound signature, and the sound of the disrupted sleep is associated with a second subject characteristic, a second group of subject characteristics, or a second subject sound signature.

In response to identifying at least one subject characteristic associated with the subject sound data collected during the sleep interval, the system may compare the at least one subject characteristic to at least one sample characteristic of the plurality of sample sleep events (or a subset thereof). For example, the system may compare one or more frequency characteristics and/or one or more amplitude characteristics of the subject sound data collected during the sleep interval to one or more frequency characteristics and/or one or more amplitude characteristics of the sample sound data associated with one or more sample sleep events. If the comparison yields a match, the system may determine that the subject sound data includes frequency, amplitude, or other waveform characteristics of a particular sample sleep event, which may suggest or indicate that the user experienced an occurrence of that particular sleep event during the sleep interval. Where the user experiences an occurrence of a sleep event, that experienced sleep event is referred to as a "subject sleep event," which is generally identified by matching the subject characteristic(s) of the subject sleep event to the sample characteristic(s) of the sample sleep event. Thus, the system may determine, based upon such a comparison and the resulting match, that the user experienced a subject sleep event during the sleep interval.

In some embodiments, the system may determine that the user experienced a subject sleep event (i.e., may identify the occurrence of the subject sleep event) based upon a partial or substantial match between at least one subject characteristic of the subject sound data collected during the sleep interval and at least one sample characteristic of the sample sound data associated with a sample sleep event. As used herein, a "substantial" match may be made between at least one subject characteristic of subject sound data collected during the sleep interval and at least one characteristic of sample sound data associated with a sample sleep event when the characteristics are similar (e.g., within a predefined range of each other) but not exactly the same.

The system may define a particular threshold range associated with a substantial match. If the characteristics fall within the predefined threshold range of one another, then the system may identify a substantial match. The threshold range may be variable based upon certain factors, such as user inputs. For instance, if a user of the client device indicates that a storm occurred during the sleep interval (e.g., using the app running on the client device), a threshold range associated with a storm sample sleep event (and the sample characteristics thereof) may be adjusted (e.g., expanded). In such a circumstance, the system may be more likely to identify a storm sleep event within the subject sound data. Additionally or alternatively, the system may access other data to define the threshold ranges for particular sleep events. For instance, the system may access weather data to determine the weather during a particular sleep interval and may adjust the threshold range based on the weather data. In other words, the system may leverage user-input data or otherwise accessed data to adjust the threshold range for any particular sleep event, or type of sleep event.

Further, in some embodiments, the system may compare a plurality of frequency characteristics and/or a plurality of amplitude characteristics of the sound data collected during the sleep interval (i.e., subject characteristics) to a plurality of frequency characteristics and/or a plurality of amplitude characteristics of the sound data associated with sample sleep events (i.e., sample characteristics). Specifically, the system may compare a subject sound signature associated with the sound data collected during the sleep interval to a sample sound signature of a sample sleep event. In addition, in some cases, the system may compare a subject sound signature associated with the sound data collected during the sleep interval to a plurality of sample sound signatures associated with a respective plurality of sample sleep events. If the subject sound signature associated with the sound data collected during the sleep interval matches, or substantially matches, at least one sample sound signature of a sample sleep event, the system may determine that the user experienced that sleep event during the sleep interval.

After one or more subject sleep events are identified as occurring during the sleep interval, the system may perform additional analyses associated with the sleep interval. The system may determine a duration of each identified subject sleep event. For instance, the system may determine an initial time at which the subject sleep event was occurring, based upon the initiation of the subject sound signature associated with that subject sleep event. The system may further determine a terminal time at which the subject sleep event stopped, based upon the termination of the subject sound signature associated with that subject sleep event. The duration of each subject sleep event may be no longer than the sleep interval.

The system may additionally or alternatively determine a number of occurrences of a subject sleep event. For instance, the system may determine that a subject sleep event recurs during the sleep interval (e.g., is identified more than once according to the methods described above), such as the user being restless, waking, snoring, etc. The system may then determine how many times that particular subject sleep event occurred. Additionally or alternatively, the system may determine a number of occurrences of a type or class of subject sleep event, such as how many times sleep events associated with waking or being restless occurred, how many times sleep events associated with sleep-breathing conditions occurred, and/or how many times environmental sleep events (e.g., thunderclaps, HVAC systems activating, etc.) occurred.

In some embodiments, the system may perform one or more additional analyses to identify trends or correlations associated with subject sleep events experienced during one or more sleep intervals. For instance, the system may determine that a plurality of "restless"-type sleep events were generally correlated with (e.g., occurred simultaneously or within a threshold amount of time of one another) a plurality of environmental-type sleep events, such as thunderclaps or other environmental noise. As another example, the system may process sound data (e.g., sound data that has already been analyzed or "raw" sound data) for a plurality of generally subsequent sleep intervals, such as a plurality of sleep intervals occurring over a week or a month.

The system may analyze the occurrence(s) of various subject sleep events to identify one or more trends in the user's sleep. The system may determine, for instance, (i) that fewer sleep events occur on weeknights, (ii) that the user is experiencing a greater number of a particular sleep event, or (iii) that the user experiences a higher rate of sleep events when the sleep interval is shorter (e.g., less than six hours). Moreover, the system may process user input in conjunction with the sound data to identify additional trends or correlations. For example, the user may input to the system (e.g., using the smartphone app) that they exercise on certain days, and the system may determine that fewer restless-type sleep events are experienced on those days.

The system may determine a level of sleep quality based upon the identified sleep events. The system may use one or more algorithms, equations, models, etc., to quantify the user's level of sleep quality using the identified sleep events as inputs. For example, a higher number of identified sleep events occurring during a single sleep interval may result in a lower calculated or determined level of sleep quality. The system may account for different types or classes of sleep events in determining the level of sleep quality. For instance, restless-type sleep events may contribute to a lower level of sleep quality, whereas deep-sleep-type events (e.g., regular breathing, low activity or movement) may contribute to a higher level of sleep quality, and environmental-type sleeps events may not be factored in or may be weighted lower in determining the level of sleep quality. The system may use other factors in determining the level of sleep quality, including, for example, but not limited to, a duration of the sleep interval and/or of individual sleep events, start or end time(s) of the sleep interval, user-input data identifying subjective opinions of sleep quality, etc.

The system may be configured to leverage user input to refine the machine learning algorithms. For example, a user may use the client device (e.g., the app running on the client device or the webpage accessed thereby) to indicate that one or more sleep events occurred during a sleep interval. The user may wake up in the middle of the sleep interval and provide user input indicating that they are awake. In such a circumstance, the system may associate one or more subject characteristics at the time of the waking with a "waking" sleep event. The user may identify a weather event that occurred during the night, such as a storm or excessive wind gusts. In such a circumstance, the system may adjust a threshold range for matching such weather events, such that the system is more likely to interpret subject characteristics from the subject sound data in accordance with the user's input (e.g., as associated with weather events). Moreover, the system may use any identified subject sleep event, in particular those confirmed by the user to have occurred, as a sample sleep event to refine the machine learning algorithm. Where the system has identified a subject sleep event—a sleep event experienced by the user—the system may then store subject sound data associated with the subject sleep event as sample sound data, which the system may then use to identify future occurrences of that sleep event. In one particular example, the system may use the processes described above and identify a sleep apnea sleep event during a sleep interval. As described herein, the system may generate a notification or recommendation that the user see a sleep specialist to confirm that the user is, in fact, experiencing sleep apnea. If the sleep specialist confirms that the subject sleep event was a sleep apnea sleep event, the system may store the subject sound data associated with that identified sleep apnea sleep event as a sample sleep apnea sleep event. Accordingly, when the system compares future subject sound data with the stored sample sound data, the system may more precisely identify sleep apnea sleep events by having a greater number of sleep apnea sample sounds to compare against.

In some embodiments, the system may develop a sleep pattern profile for the user that includes such details as typical or common breathing patterns for the user during different phases of sleep (e.g., falling asleep, deep sleep, waking, etc.). The system may not store user-specific data as sample sleep data that the system uses to "self-train" the machine learning algorithms, where the machine learning algorithms are applied to more than one user. If the system implements a user-specific version of the machine learning algorithm, the system may store user-specific data, including sleep pattern profiles, and leverage the user-specific data to refine the user-specific machine learning algorithm.

In certain embodiments, the system may be configured to analyze waking behavior alongside sound data collected during a sleep interval. For instance, the client device (e.g., using the smartphone app) may be configured to collect motion data during the user's waking hours that may then be analyzed for correlation with sleep events. In one particular embodiment, driving behavior data may be collected using the client device and analyzed in conjunction with the sound data collected during a sleep interval. The system may determine one or more trends or correlations between the driving behavior data and the sound data (or one or more sleep events identified therein). For instance, the system may determine that a lower quality of sleep of a sleep interval is highly correlated with more risky driving behavior data the following day (e.g., sharper cornering, more hard-braking, etc.). As another example, the client device (e.g., using the smartphone app) may be configured to collect sound and/or motion data, such as breathing pattern data, during the user's waking hours. The system may leverage a user's sleep pattern profile to analyze the user's waking behaviors. For example, the sleep pattern profile may include breathing patterns or other sounds associated with the user falling asleep. Based upon breathing pattern data collected during the user's waking hours, as compared to the sleep pattern profile, the system may determine that the user is falling asleep. If the system determines that the user is performing certain tasks, such as driving (e.g., using motion data), the system may transmit a control instruction to the client device to deliver a visual and/or audible alarm to prevent the user from falling asleep, for instance, while driving.

The system may, in addition, generate and provide a notification to the client device and/or to another device associated with the user or another party (e.g., a healthcare provider) that one or more subject sleep events occurring during the sleep interval were identified. For example, the system may provide the notification to the client device at a time after an end of the sleep interval (such that the notification does not disrupt the sleep interval). The notification may be formatted in any suitable format for receipt at the client device (or another computing device), such as an in-app message, an email message, a text message, a voice message, and/or any other visual and/or audible notification. The notification may include a description of each subject sleep event identified as occurring during the sleep interval. The notification may further describe a duration and/or number of occurrences of each identified subject sleep event. Additionally or alternatively, the notification may provide an indicator of sleep quality experienced by the user during the sleep interval, as described above. The notification may provide other information about the sleep interval, such as a date of the sleep interval, a beginning and end time of the sleep interval, weather information associated with the sleep interval, other environmental information (e.g., a temperature within the sleeping area, whether or not a white noise machine was activated, whether or not the user was using a sleep aid, whether or not the user was using a CPAP machine, etc.), and/or any other information determined by the system or provided by the user. The notification may additionally or alternatively include advice or recommendations based upon the analyses performed by the system. For instance, if the system determined a correlation between restless-type sleep events and environmental-type sleep events (as described above), the system may generate a recommendation that the user take steps to create a sound barrier to reduce the effects of the environmental-type sleep events, such as using ear plugs, using a white noise machine, or sleeping in a more sound-proofed sleeping area.

In some embodiments, the notification may be provided in association with an insurance policy or other insurance-associated notification and may include recommendations or advice that associates the user's sleep with the user's driving behavior. In such embodiments, the notification may provide recommendations that the user more carefully assess their driving behavior on days following a sleep interval with a short duration or low level of sleep quality.

In some embodiments, the notification may be provided in association with a healthcare plan or other healthcare-associated notification and may include recommendations or information about how sleep can affect the user's health. The notification may include, for instance, a recommendation to visit a sleep specialist based upon the identification of one or more subject sleep events associated with sleep apnea or another sleep condition.

Exemplary technical effects of the systems, methods, and computer-readable media described herein may include, for example: (a) training of a machine learning algorithm, such as a neural network, to identify sleep events and characteristics thereof for audio analysis of sleep sound data; and/or (b) reducing or eliminating the need for in-lab sleep analysis.

Figure 1:
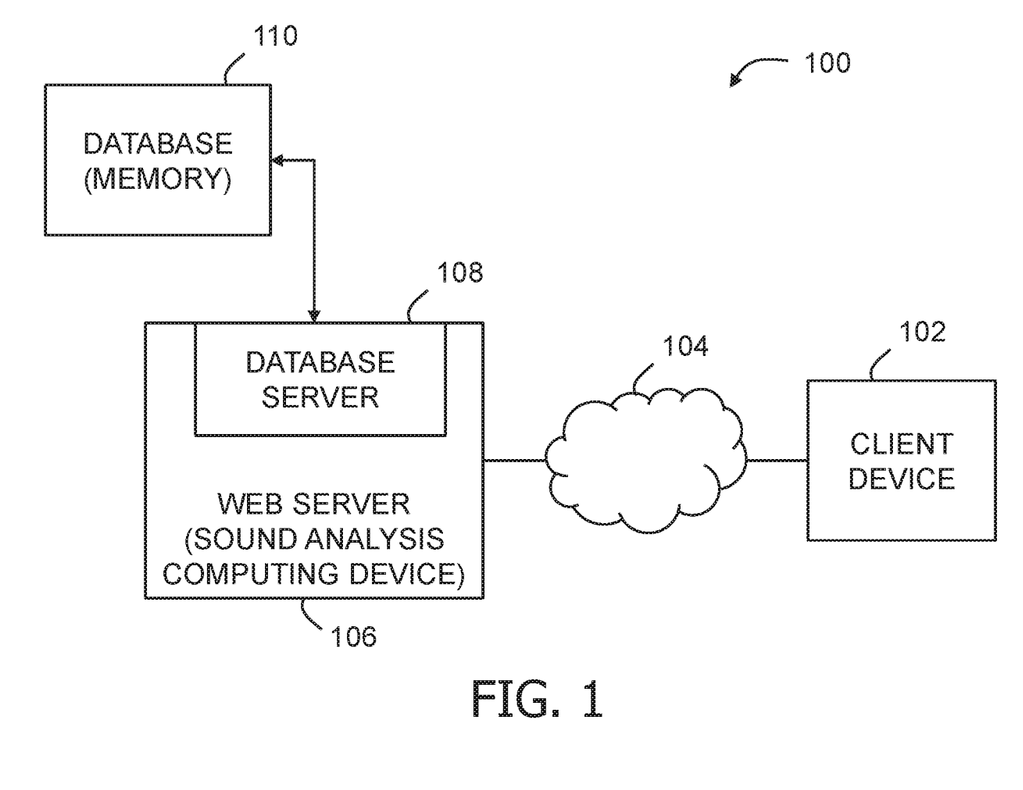
FIG. 1 illustrates a schematic diagram of an exemplary computer system for analyzing sound data associated with a user's sleep.

Exemplary System for Audio Assessment and Sound Identification to Analyze Sleep Sound Data FIG. 1 depicts a view of an exemplary system 100 for audio assessment and sound identification to analyze sound data collected during a sleep interval. In one exemplary embodiment, system 100 may include a client device, such as a client device 102. Client device 102 may be associated with an individual, such as a user who is experiencing trouble sleeping. System 100 may also include network 104, a web server 106, a database server 108, and/or a database 110.

Accordingly, in the exemplary, client device 102 may be any personal computing device and/or any mobile communications device of a user, such as a personal computer, a tablet computer, a smartphone, and the like. Client device 102 may, as described below, include one or more audio sensors (e.g., microphones) and may be configured to present an application (e.g., a smartphone "app"), which may be configured to receive, or "listen to" sound, such as ambient noise, within a sleeping area (not shown in FIG. 1) during a sleep interval. To this end, client device 102 may include or execute software for viewing and interacting with a smartphone app that receives or listens to sound within the sleeping area.

Network 104 may be any electronic communications system, such as any computer network or collection of computer networks, and may incorporate various hardware and/or software. Communication over network 104 may be accomplished via any suitable communication channels, such as, for example, one or more telephone networks, one or more extranets, one or more intranets, the Internet, one or more point of interaction devices (e.g., point of sale devices, smart phones, cellular phones), various online and/or offline communications systems, such as various local area and wide area networks, and the like.

Web server 106, which may also be referred to as a sound analysis computing device 106, may be any computer or computer system that is configured to receive and process data, such as sound data, transmitted by and received from client device 102. Web server 106 may be coupled between client device 102 and database server 108. More particularly, web server 106 may be communicatively coupled to client device 102 via network 104. In various embodiments, web server 106 may be directly coupled to database server 108 and/or communicatively coupled to database server 108 via a network, such as network 104. Web server 106 may, in addition, function to store, process, and/or deliver one or more web pages and/or any other suitable content to client device 102. Web server 106 may, in addition, receive data, such as sound data provided to the smartphone app (as described herein) and/or a webpage from client device 102 for subsequent transmission to database server 108.

In various embodiments, web server 106 may implement various hardware and/or software, such as, for example, one or more communication protocols, one or more message brokers, one or more data processing engines, one or more servlets, one or more application servers, and the like. For instance, in one embodiment, web server 106 may implement an Internet of Things (IoT) protocol, such as a machine-to-machine IoT communications protocol (e.g. an MQTT protocol). In addition, in various embodiments, web server 106 may implement a message broker program module configured to translate a message or communications from a messaging protocol of a sending device to a messaging protocol of a receiving device (e.g., RABBITTMQ, KAFKA, ACTIVEMQ, KESTREL). Further still, in some embodiments, web server 106 may implement a data processing engine, such as a cluster computing framework like APACHE SPARK. In addition, in various embodiments, web server 106 may implement servlet and/or JSP server, such as APACHE TOMCAT.

Database server 108 may be any computer or computer program that provides database services to one or more other computers or computer programs. In various embodiments, database server 108 may be communicatively coupled between web server 108 and database 110. Database server 108 may, in addition, function to process data received from web server 106, such as sound data, which may include, for example, sound data received from client device 102.

In various embodiments, web server 106 and/or database server 108 may train and/or implement one or more machine learning algorithms, as described herein, to process sound data, such as sound data stored within database 110. For example, in some embodiments, web server 106 and/or database server 108 may process sound data associated with a known or "sample" sleep events, to identify one or more sample characteristics associated with each sample sleep event. Such sample characteristics may include any characteristics or features associated with the respective sample sleep event, such as frequency characteristics, amplitude characteristics, and/or any other waveform characteristics of the sound data (which may be digital or analog) of one or more sample sleep events. In some embodiments, web server 106 and/or database server 108 may identify a sample sound "signature" or a sample sound "fingerprint" associated with one or more sample sleep events. A sample sound signature of sample sleep event may include a plurality of waveform or other characteristics associated with the sample sleep event and may function to uniquely identify the sample sleep event.

Database 110 may be any organized collection of data, such as, for example, any data organized as part of a relational data structure, any data organized as part of a flat file, and the like. Database 110 may be communicatively coupled to database server 108 and may receive data from, and provide data to, database server 108, such as in response to one or more requests for data, which may be provided via a database management system (DBMS) implemented on database server 108. In various embodiments, database 110 may be a non-relational database, such as an APACHE HADOOP database.

Although the components of system 100 are described below and depicted at FIG. 1 as being interconnected in a particular configuration, it is contemplated that the systems, subsystems, hardware and software components, various network components, and database systems described herein may be variously configured and interconnected and may communicate with one another within system 100 to facilitate the processes and advantages described herein. For example, although a single web server 106, a single database server 108, and a single database 110 are described above, it will be appreciated that system 100 may include any suitable number of interconnected, communicatively coupled, web servers, database servers, and/or databases. Further, although certain functions, processes, and operations are described herein with respect to one or more system components, it is contemplated that one or more other system components may perform the functions, processes, and operations described herein.

Exemplary Client Device

Figure 2:
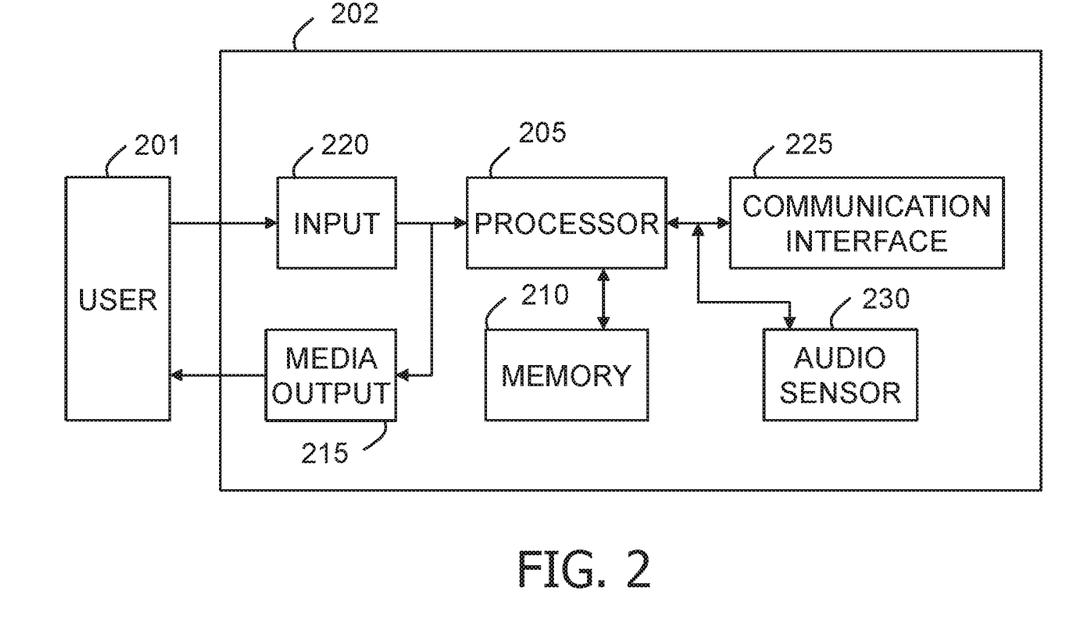
FIG. 2 illustrates an exemplary configuration of a client device shown in FIG. 1, in accordance with one embodiment of the present disclosure.

FIG. 2 depicts an exemplary configuration of a client device 202, such as client device 102, as shown in FIG. 1, and in accordance with one embodiment of the present disclosure. Client device 202 may be operated by a user 201. Client device 202 may include a processor 205 for executing instructions. In some embodiments, executable instructions may be stored in a memory area 210. Processor 205 may include one or more processing units (e.g., in a multi-core configuration). Memory area 210 may be any device allowing information such as executable instructions and/or sound data to be stored and retrieved. Memory area 210 may include one or more computer readable media.

Client device 202 may also include at least one media output component 215 for presenting information to user 201. Media output component 215 may be any component capable of conveying information to user 201. In some embodiments, media output component 215 may include an output adapter (not shown) such as a video adapter and/or an audio adapter. An output adapter may be operatively coupled to processor 205 and adapted to operatively couple to an output device such as a display device (e.g., a cathode ray tube (CRT), liquid crystal display (LCD), light emitting diode (LED) display, or "electronic ink" display) or an audio output device (e.g., a speaker or headphones).

In some embodiments, media output component 215 may be configured to present a graphical user interface (e.g., a web browser and/or a client application) to user 201. A graphical user interface may include, for example, an online store interface for viewing and/or purchasing items, and/or a wallet application for managing payment information. In some embodiments, client device 202 may include an input device 220 for receiving input from user 201. User 201 may use input device 220 to, without limitation, select and/or enter data, such as, for example, subjective opinions of sleep quality, "diary" entries of behavior or events during waking hours, etc.

Input device 220 may include, for example, a keyboard, a pointing device, a mouse, a stylus, a touch sensitive panel (e.g., a touch pad or a touch screen), a gyroscope, an accelerometer, a position detector, a biometric input device, and/or an audio input device or audio sensor. A single component such as a touch screen may function as both an output device of media output component 215 and input device 220.

Client device 202 may also include a communication interface 225, communicatively coupled via network 104 to web server 106 (shown in FIG. 1). Communication interface 225 may include, for example, a wired or wireless network adapter and/or a wireless data transceiver for use with a mobile telecommunications network.

Stored in memory area 210 are, for example, computer readable instructions for providing a user interface to user 201 via media output component 215 and, optionally, receiving and processing input from input device 220. A user interface may include, among other possibilities, a web browser and/or a client application. Web browsers enable users, such as user 201, to display and interact with media and other information typically embedded on a web page or a website.

Client device 202 may also include one or more audio sensors, such as audio sensor 230. Audio sensor 230 may be any suitable audio sensor, such as a microphone, for receiving and/or collecting sound data during a sleep interval. Audio sensor 230 may be communicatively coupled to processor 205, which may implement an analog to digital converter in software to convert analog sound data received by audio sensor 230 to digital data. In some embodiments, client device 202 may include a separate (e.g., hardware and/or software) analog to digital converter coupled between audio sensor 230 and processor 205. Moreover, in some embodiments, audio sensor 230 may be separate from and communicatively coupled to client device 202. For instance, audio sensor 230 may be embodied as a separate microphone in wired connection with or wirelessly connected to client device 202.

Exemplary Database System

Figure 3:
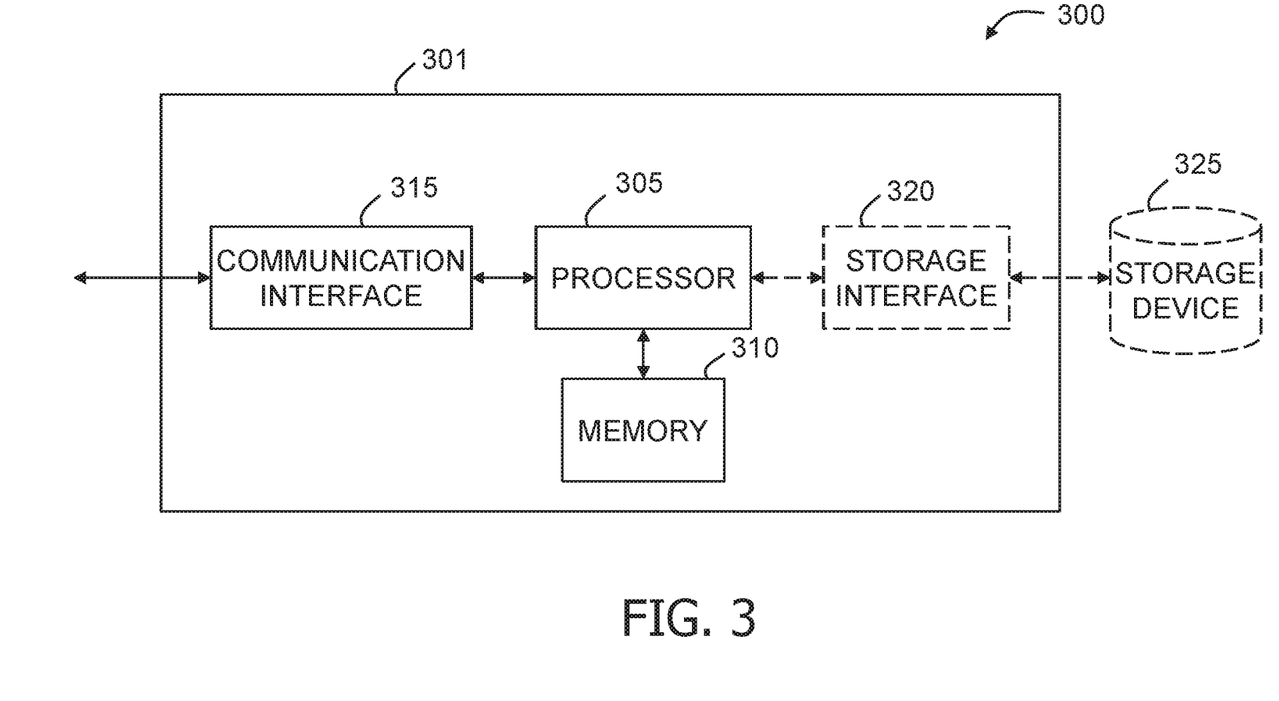
FIG. 3 illustrates an exemplary configuration of a server shown in FIG. 1, in accordance with one embodiment of the present disclosure.

FIG. 3 depicts an exemplary database system 300 such as database server 108 and database 110, as shown in FIG. 1, and in accordance with one exemplary embodiment of the present disclosure. Accordingly, database system 300 may include a server computer device 301 (e.g., web server 106 or database server 108, shown in FIG. 1), which may, in turn, include a processor 305 for executing instructions. Instructions may be stored in a memory area 310. Processor 305 may include one or more processing units (e.g., in a multi-core configuration).

Processor 305 may be operatively coupled to a communication interface 315 such that server computer device 301 is capable of communicating with a remote computing device, as described above. For example, communication interface 315 may receive requests from client device 202 via the Internet and/or over a computer network.

Processor 305 may also be operatively coupled to a storage device 325 (e.g., database 110). Storage device 325 may be any computer-operated hardware suitable for storing and/or retrieving data, such as, but not limited to, data associated with database 110. In some embodiments, storage device 325 may be integrated in server computer device 301. For example, server computer device 301 may include one or more hard disk drives as storage device 325.

In other embodiments, storage device 325 may be external to server computer device 301 and may be accessed by a plurality of server computer devices 301. For example, storage device 325 may include a storage area network (SAN), a network attached storage (NAS) system, and/or multiple storage units such as hard disks and/or solid state disks in a redundant array of inexpensive disks (RAID) configuration.

In some embodiments, processor 305 may be operatively coupled to storage device 325 via a storage interface 320. Storage interface 320 may be any component capable of providing processor 305 with access to storage device 325. Storage interface 320 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 305 with access to storage device 325.

Figure 4:
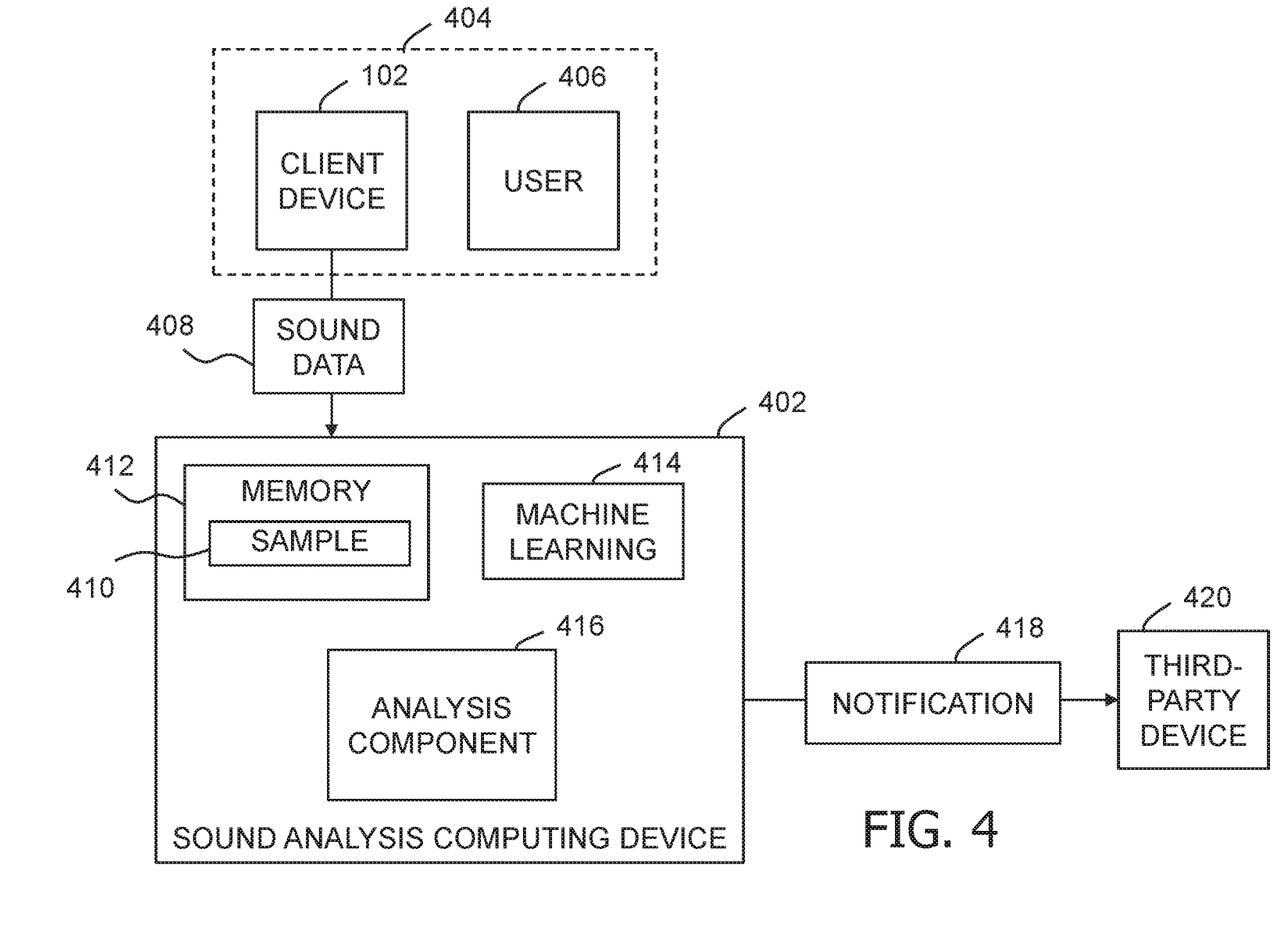
FIG. 4 is a data flow diagram illustrating the flow of data between components of the computer system shown in FIG. 1.

Exemplary Process for Monitoring Sound to Analyze a User's Sleep Using Machine Learning Techniques FIG. 4 is a data flow diagram 400 illustrating the flow of data between components of the computer system 100 illustrated in FIG. 1, specifically to and from a sound analysis computing device 402, which may include and/or be similar to web server 106 (shown in FIG. 1). In the exemplary embodiment, computer system 100 includes sound analysis computing device 402. Sound analysis computing device 402 may include and/or be similar to web server 106, such that sound analysis computing device 402 represents a back-end computing device of computer system 100. Alternatively, sound analysis computing device 402 may include client device 102. In other words, the sound analysis processes described herein may be implemented on client device 102, either completely and/or by accessing web server 106 and/or another back-end computing device (e.g., to access one or more machine learning algorithms). In the illustrated embodiment, sound analysis computing device 402 is separate from and in communication with client device 102 (e.g., over network 104, shown in FIG. 1).

Specifically, client device 102 is located within a sleeping area 404 (e.g., a bedroom or other sleeping area) of a user 406 (which may be user 201, shown in FIG. 2) during one or more sleep intervals of user 406. In particular, client device 102 is located within a threshold distance of user 406 during the sleep interval, such that client device 102 may capture sound data 408 during the sleep interval. Client device 102 may be running an app (and/or may be providing a webpage) that facilitates collection of sound data 408 during a sleep interval and subsequent transmittal of sound data 408 to sound analysis computing device 402. The app may facilitate additional functionality, such as permitting user 406 to enter user input (as described herein) and enabling user 406 to receive and view notifications.

Sound analysis computing device 402 may compare one or more characteristics of sound data 408 collected during the sleep interval ("subject characteristics") to one or more characteristics associated with known sleep events ("sample characteristics") to identify one or more sleep events that occur during the sleep interval ("subject sleep events"). Such comparison may provide user 406 insight into one or more sleep conditions or issues user 406 is experiencing, which may facilitate improving the user's sleep.

In the exemplary embodiment, sound analysis computing device 402 may analyze sample sound data 410 associated with a plurality of known sleep events, also referred to as "sample sleep events." Sample sound data 410 may be stored in a memory 412 of sound analysis computing device 402. Memory 412 may include and/or be similar to database 110 (shown in FIG. 1). Sample sleep events may include, for instance, sleep disorders (e.g., sleep apnea, insomnia, sleep movement disorder, snoring, parasomnia, etc.), sleep stages (e.g., falling asleep, light sleep, rapid eye movement (REM) sleep, waking), environmental factors or conditions (e.g., white noise, weather sounds, etc.), and/or other events that may occur during a user's sleep interval. Sample sound data 410 may include digital and/or analog sound data associated with the plurality of sample sleep events.

Sound analysis computing device 402 may perform the processes described herein using one or more machine learning algorithms 414, such as one or more machine learning algorithms 414 configured to identify one or more characteristics associated with each of the sample sleep events. Stored sample sound data 410 may include a plurality of sound files associated with respective sample sleep events. In one embodiment, a user associated with training machine learning algorithm(s) 414, referred to as an "expert user," may indicate the content of each sound file. For instance, the expert user may indicate that one set of sound files contains sample sound data 410 of sleep condition sleep events, such as a person experiencing sleep apnea.

Each sample sleep event may be associated with one or more characteristics, such as frequency characteristics, amplitude characteristics, various other waveform characteristics, duration characteristics, and the like. The sample characteristics may be identified by sound analysis computing device 402 (e.g., by training and/or implementing one or more machine learning algorithms 414) or may be identified by the expert user to sound analysis computing device 402 (e.g., during a training phase for machine learning algorithms 414). For example, the expert user may identify one or more characteristics of a sleep apnea sleep event (i.e., the sound(s) made during a sleep apnea sleep event). Additionally or alternatively, the expert user may indicate the content of a sound file of the sample sleep event, and sound analysis computing device 402 may "self-learn" one or more characteristics associated with that sample sleep event. Thus, sound analysis computing device 402 may identify, based upon an analysis of sample sound data 410 associated with one or more sleep events, one or more characteristics, such as at least a first "sample characteristic," associated with one or more sample sleep events. Where a particular sample sleep event is associated with a plurality of sample characteristics, these sample characteristics may collectively be referred to as a unique sample sound "signature" or sample sleep event signature. It should be readily understood that certain sample characteristics may be common to a plurality of the sample sleep events (e.g., particular breathing patterns or levels), but that sample sound signatures include a particular set of characteristics that uniquely identify that sample sleep event.

During or after a sleep interval, sound analysis computing device 402 may, in addition, receive, from client device 102, sound data 408 (also referred to as "subject sound data"), such as ambient sound data, collected by client device 102 within sleeping area 404. More particularly, a smartphone app, as described above, running on client device 102 may "listen" to or detect the sound within sleeping area 404. Client device 102 may, in addition, include an analog to digital converter, which may convert analog sound data collected by client device 102 to digital subject sound data 408.

In response to receiving subject sound data 408 from client device 102, sound analysis computing device 402 may analyze subject sound data 408. Sound analysis computing device 402 may include one or more analysis component(s) 416 configured to perform these analyses. Analysis component 416 may include specific computer-executable instructions causing sound analysis computing device 402 to perform the processes described herein. Alternatively, analysis component 416 may include a separate processing component specifically programmed to perform the processes described herein. More particularly, sound analysis computing device 402 may analyze subject sound data 408 collected during the sleep interval to identify one or more characteristics, such as at least a first "subject characteristic," of subject sound data 408. These subject characteristics may include frequency characteristics, amplitude characteristics, various other waveform characteristics, and the like, associated with the user's sleep during the sleep interval. Further, where a plurality of subject characteristics are identified in conjunction with subject sound data 408, the sound characteristics may collectively define a subject sound signature.

In addition, in some cases, sound analysis computing device 402 may identify a plurality of groups of characteristics or a plurality of sound signatures within subject sound data 408, such that subject sound data 408 actually includes a plurality of sound signatures. This may occur, for example, as a result of a plurality of distinct sleep events occurring during the sleep interval, such as a first sleep event associated with disrupted sleep and a second sleep event associated with a thunderstorm. Certain sounds may, in other words, intermingle or intermix with one or more other sounds during the sleep interval. Sound analysis computing device 402 may, under such a circumstance, identify characteristics associated with both sounds, such that the thunderstorm during the sleep interval is associated with a first subject characteristic, a first group of subject characteristics, or a first subject sound signature, and the sound of the disrupted sleep is associated with a second subject characteristic, a second group of subject characteristics, or a second subject sound signature.

In response to identifying at least one characteristic associated with subject sound data 408, sound analysis computing device 402 may compare the at least one subject characteristic to at least one sample characteristic of the plurality of sample sleep events (or a subset thereof). For example, sound analysis computing device 402 may compare one or more frequency characteristics and/or one or more amplitude characteristics of subject sound data 408 to one or more frequency characteristics and/or one or more amplitude characteristics of sample sound data 410 associated with one or more sample sleep events. If the comparison yields a match, sound analysis computing device 402 may determine that subject sound data 408 includes frequency, amplitude, or other waveform characteristics of a particular sample sleep event, which may suggest or indicate that user 406 experienced an occurrence of that particular sleep event during the sleep interval. Where user 406 experiences an occurrence of a sleep event, that experienced sleep event is referred to as a "subject sleep event," which is generally identified by matching the subject characteristic(s) of the subject sleep event to the sample characteristic(s) of the sample sleep event. Thus, sound analysis computing device 402 may determine, based upon such a comparison and the resulting match, that user 406 experienced a subject sleep event during the sleep interval.

In some embodiments, sound analysis computing device 402 may determine that the user experienced a subject sleep event (i.e., may identify the occurrence of the subject sleep event) based upon a partial or substantial match between at least one subject characteristic of subject sound data 408 and at least one sample characteristic of sample sound data 410. As used herein, a "substantial" match may be made between at least one subject characteristic of subject sound data 408 and at least one characteristic of sample sound data 410 when the characteristics are similar (e.g., within a predefined range of each other) but not exactly the same.

Sound analysis computing device 402 may define a particular threshold range associated with a substantial match. If the characteristics fall within the predefined threshold range of one another, then sound analysis computing device 402 may identify a substantial match. The threshold range may be variable based upon certain factors, such as user inputs. For instance, if user 406 of client device 102 indicates that a storm occurred during the sleep interval (e.g., using the app running on client device 102), a threshold range associated with a storm sample sleep event (and the sample characteristics thereof) may be adjusted (e.g., expanded). In such a circumstance, sound analysis computing device 402 may be more likely to identify a storm sleep event within subject sound data 408. Additionally or alternatively, sound analysis computing device 402 may access other data to define the threshold ranges for particular sleep events. For instance, sound analysis computing device 402 may access weather data to determine the weather during a particular sleep interval and may adjust the threshold range based on the weather data. In other words, sound analysis computing device 402 may leverage user-input data or otherwise accessed data to adjust the threshold range for any particular sleep event, or type of sleep event.

Further, in some embodiments, sound analysis computing device 402 may compare a plurality of frequency characteristics and/or a plurality of amplitude characteristics of subject sound data 408 (i.e., subject characteristics) to a plurality of frequency characteristics and/or a plurality of amplitude characteristics of sample sound data 410 (i.e., sample characteristics). Specifically, sound analysis computing device 402 may compare a subject sound signature associated with subject sound data 408 to a sample sound signature of a sample sleep event. In addition, in some cases, sound analysis computing device 402 may compare a subject sound signature associated with subject sound data 408 to a plurality of sample sound signatures associated with a respective plurality of sample sleep events. If the subject sound signature associated with subject sound data 408 matches, or substantially matches, at least one sample sound signature of a sample sleep event, sound analysis computing device 402 may determine that user 406 experienced that sleep event during the sleep interval.

After one or more subject sleep events are identified as occurring during the sleep interval, sound analysis computing device 402 may perform additional analyses associated with the sleep interval. Sound analysis computing device 402 may determine a duration of each identified subject sleep event. For instance, sound analysis computing device 402 may determine an initial time at which the subject sleep event was occurring, based upon the initiation of the subject sound signature associated with that subject sleep event. Sound analysis computing device 402 may further determine a terminal time at which the subject sleep event stopped, based upon the termination of the subject sound signature associated with that subject sleep event. The duration of each subject sleep event may be no longer than the sleep interval.

Sound analysis computing device 402 may additionally or alternatively determine a number of occurrences of a subject sleep event. For instance, sound analysis computing device 402 may determine that a subject sleep event recurs during the sleep interval (e.g., is identified more than once according to the methods described above), such as the user being restless, waking, snoring, etc. Sound analysis computing device 402 may then determine how many times that particular subject sleep event occurred. Additionally or alternatively, sound analysis computing device 402 may determine a number of occurrences of a type or class of subject sleep event, such as how many times sleep events associated with waking or being restless occurred, how many times sleep events associated with sleep-breathing conditions occurred, and/or how many times environmental sleep events (e.g., thunderclaps, HVAC systems activating, etc.) occurred.

In some embodiments, sound analysis computing device 402 may perform one or more additional analyses to identify trends or correlations associated with subject sleep events experienced during one or more sleep intervals. For instance, sound analysis computing device 402 may determine that a plurality of "restless"-type sleep events were generally correlated with (e.g., occurred simultaneously or within a threshold amount of time of one another) a plurality of environmental-type sleep events, such as thunderclaps or other environmental noise. As another example, sound analysis computing device 402 may process subject sound data 408 collected during a plurality of generally subsequent sleep intervals, such as a plurality of sleep intervals occurring over a week or a month. Sound analysis computing device 402 may analyze the occurrence(s) of various subject sleep events to identify one or more trends in the user's sleep. Sound analysis computing device 402 may determine that fewer sleep events occur on weeknights, that user 406 is experiencing a greater number of a particular sleep event, or that user 406 experiences a higher rate of sleep events when the sleep interval is shorter (e.g., less than six hours). Moreover, sound analysis computing device 402 may process user input in conjunction with subject sound data 408 to identify additional trends or correlations. For example, user 406 may input to sound analysis computing device 402 (e.g., using the smartphone app) that they exercise on certain days, and sound analysis computing device 402 may determine that fewer restless-type sleep events are experienced on those days.

Sound analysis computing device 402 may determine a level of sleep quality based upon the identified sleep events. Sound analysis computing device 402 may use one or more algorithms, equations, models, etc., to quantify the user's level of sleep quality using the identified sleep events as inputs. For example, a higher number of identified sleep events occurring during a single sleep interval may result in a lower calculated or determined level of sleep quality. Sound analysis computing device 402 may account for different types or classes of sleep events in determining the level of sleep quality. For instance, restless-type sleep events may contribute to a lower level of sleep quality, whereas deep-sleep-type events (e.g., regular breathing, low activity or movement) may contribute to a higher level of sleep quality, and environmental-type sleeps events may not be factored in or may be weighted lower in determining the level of sleep quality. Sound analysis computing device 402 may use other factors in determining the level of sleep quality, including, for example, but not limited to, a duration of the sleep interval and/or of individual sleep events, start or end time(s) of the sleep interval, user-input data identifying subjective opinions of sleep quality, etc.

Sound analysis computing device 402 may be configured to leverage user input to refine machine learning algorithms 414. For example, user 406 may use client device 102 (e.g., the app running on client device 102 or the webpage accessed thereby) to indicate that one or more sleep events occurred during a sleep interval. User 406 may wake up in the middle of the sleep interval and provide user input indicating that they are awake. In such a circumstance, sound analysis computing device 402 may associate one or more subject characteristics at the time of the waking with a "waking" sleep event. User 406 may identify a weather event that occurred during the night, such as a storm or excessive wind gusts. In such a circumstance, sound analysis computing device 402 may adjust a threshold range for matching such weather events, such that sound analysis computing device 402 is more likely to interpret subject characteristics from subject sound data 408 in accordance with the user's input (e.g., as associated with weather events). Moreover, sound analysis computing device 402 may use any identified subject sleep event, in particular those confirmed by user 406 to have occurred, as a sample sleep event to refine machine learning algorithms 414. Where sound analysis computing device 402 has identified a subject sleep event—a sleep event experienced by user 406—sound analysis computing device 402 may then store subject sound data 408 associated with the subject sleep event as sample sound data 410, which sound analysis computing device 402 may then use to identify future occurrences of that sleep event. In one particular example, sound analysis computing device 402 may use the processes described above and identify a sleep apnea sleep event during a sleep interval. As described herein, sound analysis computing device 402 may generate a notification or recommendation that user 406 see a sleep specialist to confirm that user 406 is, in fact, experiencing sleep apnea. If the sleep specialist confirms that the subject sleep event was a sleep apnea sleep event, sound analysis computing device 402 may store subject sound data 408 associated with that identified sleep apnea sleep event as a sample sleep apnea sleep event. Accordingly, when sound analysis computing device 402 compares future subject sound data (not specifically shown) with stored sample sound data 410, sound analysis computing device 402 may more precisely identify sleep apnea sleep events by having a greater number of sleep apnea sample sounds to compare against.

In some embodiments, sound analysis computing device 402 may develop a sleep pattern profile for user 406 that includes such details as typical or common breathing patterns for user 406 during different phases of sleep (e.g., falling asleep, deep sleep, waking, etc.). Sound analysis computing device 402 may not store user-specific data as sample sleep data 410 that sound analysis computing device 402 uses to "self-train" machine learning algorithms 414, where machine learning algorithms 414 are applied to more than one user. If sound analysis computing device 402 implements a user-specific version of machine learning algorithm 414, sound analysis computing device 402 may store user-specific data (e.g., as sample sound data 410), including sleep pattern profiles, and leverage the user-specific data to refine the user-specific machine learning algorithm 414.

In certain embodiments, sound analysis computing device 402 may be configured to analyze waking behavior alongside subject sound data 408. For instance, client device 102 (e.g., using the smartphone app) may be configured to collect motion data (not shown) during the user's waking hours that may then be analyzed for correlation with sleep events. In one particular embodiment, driving behavior data (not shown) may be collected using client device 102 and analyzed in conjunction with subject sound data 408. Sound analysis computing device 402 may determine one or more trends or correlations between the driving behavior data and subject sound data 408 (or one or more sleep events identified therein). For instance, sound analysis computing device 402 may determine that a lower quality of sleep of a sleep interval is highly correlated with more risky driving behavior data the following day (e.g., sharper cornering, more hard-braking, etc.). As another example, client device 102 (e.g., using the smartphone app) may be configured to collect sound and/or motion data, such as breathing pattern data, during the user's waking hours. Sound analysis computing device 402 may leverage a user's sleep pattern profile to analyze the user's waking behaviors. For example, the sleep pattern profile may include breathing patterns or other sounds associated with user 406 falling asleep. Based upon breathing pattern data collected during the user's waking hours, as compared to the sleep pattern profile, sound analysis computing device 402 may determine that user 406 is falling asleep. If sound analysis computing device 402 determines that user 406 is performing certain tasks, such as driving (e.g., using motion data), sound analysis computing device 402 may transmit a control instruction to client device 102 to deliver a visual and/or audible alarm to prevent user 406 from falling asleep, for instance, while driving.

Sound analysis computing device 402 may, in addition, generate and provide a notification 418 to client device 102 and/or (with user consent) to a third-party device 420 associated with another party (e.g., a healthcare provider) that one or more subject sleep events occurring during the sleep interval were identified. For example, sound analysis computing device 402 may provide notification 418 to client device 102 at a time after an end of the sleep interval (such that the notification does not disrupt the sleep interval). Notification 418 may be formatted in any suitable format for receipt at client device 102 (or third-party device 420), such as an in-app message, an email message, a text message, a voice message, and/or any other visual and/or audible notification. Notification 418 may include a description of each subject sleep event identified as occurring during the sleep interval. Notification 418 may further describe a duration and/or number of occurrences of each identified subject sleep event. Additionally or alternatively, notification 418 may provide an indicator of sleep quality experienced by user 406 during the sleep interval, as described above. Notification 418 may provide other information about the sleep interval, such as a date of the sleep interval, a beginning and end time of the sleep interval, weather information associated with the sleep interval, other environmental information (e.g., a temperature within sleeping area 404, whether or not a white noise machine was activated, whether or not user 406 was using a sleep aid, whether or not user 406 was using a CPAP machine, etc.), and/or any other information determined by sound analysis computing device 402 or provided by user 406. Notification 418 may additionally or alternatively include advice or recommendations based upon the analyses performed by sound analysis computing device 402. For instance, if sound analysis computing device 402 determined a correlation between restless-type sleep events and environmental-type sleep events (as described above), sound analysis computing device 402 may generate a recommendation that user 406 take steps to create a sound barrier to reduce the effects of the environmental-type sleep events, such as using ear plugs, using a white noise machine, or sleeping in a more sound-proofed sleeping area 404.

In some embodiments, notification 418 may be provided in association with an insurance policy or other insurance-associated notification and may include recommendations or advice that associates the user's sleep with the user's driving behavior. In such embodiments, notification 418 may provide recommendations that user 406 more carefully assess their driving behavior on days following a sleep interval with a short duration or low level of sleep quality.

In some embodiments, notification 418 may be provided in association with a healthcare plan or other healthcare-associated notification and may include recommendations or information about how sleep can affect the user's health. Notification 418 may include, for instance, a recommendation to visit a sleep specialist based upon the identification of one or more subject sleep events associated with sleep apnea or another sleep condition.

Figure 5:
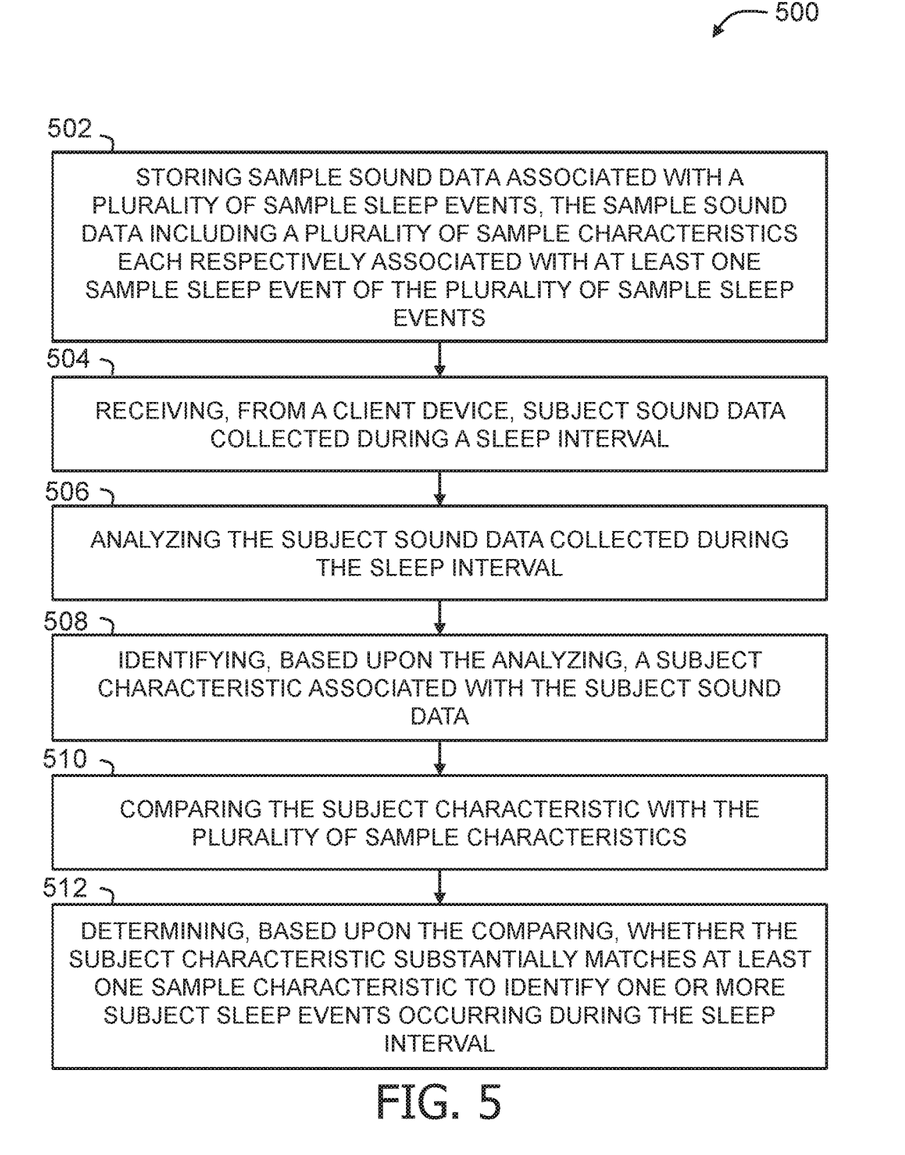
FIG. 5 illustrates an exemplary process implemented by the computer system shown in FIG. 1 for assessing sound to analyze a user's sleep using machine learning techniques.

FIG. 5 depicts a flowchart of an exemplary process 500 for assessing sound to analyze a user's sleep using machine learning techniques, process 500 implemented by computer system 100, such as web server 106, and/or by sound analysis computing device 402.

In the exemplary embodiment, process 500 may include storing 502 sample sound data (e.g., sample sound data 410, shown in FIG. 4) associated with a plurality of sample sleep events, the sample sound data including a plurality of sample characteristics each respectively associated with at least one sample sleep event of the plurality of sample sleep events. Process 500 may also include receiving 504, from a client device (e.g., client device 102, shown in FIG. 1), subject sound data (e.g., subject sound data 408, shown in FIG. 4) collected during a sleep interval. Process 500 may include analyzing 506 the subject sound data collected during the sleep interval, and identifying 508, based upon analyzing 506, a subject characteristic associated with the subject sound data. Process 500 may still further include comparing 510 the subject characteristic with the plurality of sample characteristics, as well as determining 512, based upon comparing 510, whether the subject characteristic substantially matches at least one sample characteristic to identify one or more subject sleep events occurring during the sleep interval.

Process 500 may include additional, fewer, and/or alternative steps, including those described elsewhere herein. For instance, in some embodiments, process 500 may include generating, based upon the identified one or more subject sleep events, a notification describing the one or more sleep events, and transmitting the notification to the client device. Process 500 may include determining a duration of each identified subject sleep event. Process 500 may include determining that a first subject sleep event recurs during the sleep interval, and determining a number of occurrences of the first subject sleep event. In some embodiments, process 500 may include determining a number of subject sleep events that occurred during the sleep interval, and determining a level of sleep quality associated with the sleep interval based upon the number of subject sleep events. In some embodiments, process 500 may further include identifying one or more subject sleep events occurring over a plurality of sleep intervals based upon respective subject sound data for each sleep interval of the plurality of sleep intervals, identifying at least one sleep trend associated with the plurality of sleep intervals, generating a notification describing the at least one sleep trend, and transmitting the notification to the client device.

In some embodiments, receiving 504 subject sound data may include receiving the subject sound data from at least one audio sensor associated with the client device. In some embodiments, receiving 504 subject sound data may include receiving the subject sound data from the client device positioned at a location within a threshold distance of the user during the sleep interval.

EXEMPLARY EMBODIMENTS & FUNCTIONALITY

In one aspect, a computer-based method for assessing sound to analyze a user's sleep is described. The method may be performed using a sound analysis computing device including at least one processor in communication with at least one memory device. The method may include: (i) storing sample sound data associated with a plurality of sample sleep events, the sample sound data including a plurality of sample characteristics each respectively associated with at least one sample sleep event of the plurality of sample sleep events; (ii) receiving, from a client device, subject sound data collected during a sleep interval; (iii) analyzing, using a machine learning algorithm, the subject sound data collected during the sleep interval; (iv) identifying, based upon the analyzing, a subject characteristic associated with the subject sound data; (v) comparing the subject characteristic with the plurality of sample characteristics; and/or (vi) determining, based upon the comparing, whether the subject characteristic substantially matches at least one sample characteristic to identify one or more subject sleep events occurring during the sleep interval.

In another aspect, a computer system for assessing sound to analyze a user's sleep is described. The computer system includes a processor, and a non-transitory, tangible, computer-readable storage medium having instructions stored thereon that, in response to execution by the processor, cause the processor to perform operations including: (i) storing sample sound data associated with a plurality of sample sleep events, the sample sound data including a plurality of sample characteristics each respectively associated with at least one sample sleep event of the plurality of sample sleep events; (ii) receiving, from a client device, subject sound data collected during a sleep interval; (iii) analyzing, using a machine learning algorithm, the subject sound data collected during the sleep interval; (iv) identifying, based upon the analyzing, a subject characteristic associated with the subject sound data; (v) comparing the subject characteristic with the plurality of sample characteristics; and/or (vi) determining, based upon the comparing, whether the subject characteristic substantially matches at least one sample characteristic to identify one or more subject sleep events occurring during the sleep interval.

In yet another aspect, a non-transitory computer readable medium that includes executable instructions for assessing sound to analyze a user's sleep is described. When executed by a sound analysis computing device including at least one processor in communication with at least one memory device, the computer executable instructions may cause the sound analysis computing device to: (i) store sample sound data associated with a plurality of sample sleep events, the sample sound data including a plurality of sample characteristics each respectively associated with at least one sample sleep event of the plurality of sample sleep events; (ii) receive, from a client device, subject sound data collected during a sleep interval; (iii) analyze, using a machine learning algorithm, the subject sound data collected during the sleep interval; (iv) identify, based upon the analysis, a subject characteristic associated with the subject sound data; (v) compare the subject characteristic with the plurality of sample characteristics; and/or (vi) determine, based upon the comparison, whether the subject characteristic substantially matches at least one sample characteristic to identify one or more subject sleep events occurring during the sleep interval.

Machine Learning & Other Matters

The computer-implemented methods discussed herein may include additional, less, or alternate actions, including those discussed elsewhere herein. The methods may be implemented via one or more local or remote processors, transceivers, servers, and/or sensors (such as processors, transceivers, servers, and/or sensors mounted on vehicles or mobile devices, or associated with smart infrastructure or remote servers), and/or via computer-executable instructions stored on non-transitory computer-readable media or medium.

Additionally, the computer systems discussed herein may include additional, less, or alternate functionality, including that discussed elsewhere herein. The computer systems discussed herein may include or be implemented via computer-executable instructions stored on non-transitory computer-readable media or medium.

A processor or a processing element may be trained using supervised or unsupervised machine learning, and the machine learning program may employ a neural network, which may be a convolutional neural network, a deep learning neural network, or a combined learning module or program that learns in two or more fields or areas of interest. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample data sets or certain data into the programs, such as sample audio files of known sounds. The machine learning programs may utilize deep learning algorithms that may be primarily focused on audio pattern recognition, and may be trained after processing multiple examples. The machine learning programs may include Bayesian program learning (BPL), audio/sound/voice recognition and synthesis, Hidden Markov Models (HMM), vector quantization, feature extraction, k-means algorithms, natural language processing, semantic analysis, automatic reasoning, kernel density estimation of probability (KDE), and/or other machine learning techniques—either individually or in combination.

In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs.

ADDITIONAL CONSIDERATIONS

As will be appreciated based upon the foregoing specification, the above-described embodiments of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one embodiment, a computer program is provided, and the program is embodied on a computer readable medium. In an exemplary embodiment, the system is executed on a single computer system, without requiring a connection to a sever computer. In a further embodiment, the system is being run in a Windows® environment (Windows is a registered trademark of Microsoft Corporation, Redmond, Wash.). In yet another embodiment, the system is run on a mainframe environment and a UNIX® server environment (UNIX is a registered trademark of X/Open Company Limited located in Reading, Berkshire, United Kingdom). The application is flexible and designed to run in various different environments without compromising any major functionality.

In some embodiments, the system includes multiple components distributed among a plurality of computing devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes. The present embodiments may enhance the functionality and functioning of computers and/or computer systems.

As used herein, an element or step recited in the singular and preceded by the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional embodiments that also incorporate the recited features.

The patent claims at the end of this document are not intended to be construed under 35 U.S.C. § 112(f) unless traditional means-plus-function language is expressly recited, such as "means for" or "step for" language being expressly recited in the claim(s).

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A computer-based method for assessing sound to analyze a user's sleep, the method performed using a sound analysis computing device comprising at least one processor in communication with at least one memory device, the method comprising:
   storing sample sound data associated with a plurality of sample sleep events, the sample sound data including a plurality of sample characteristics each respectively associated with at least one sample sleep event of the plurality of sample sleep events;
   receiving, from a client device, subject sound data collected during a sleep interval;
   analyzing, using a machine learning algorithm, the subject sound data collected during the sleep interval;
   identifying, based upon the analyzing, a subject characteristic associated with the subject sound data;
   comparing the subject characteristic with the plurality of sample characteristics; and
   determining, based upon the comparing, whether the subject characteristic substantially matches at least one sample characteristic to identify one or more subject sleep events occurring during the sleep interval.

2. The method of claim 1 further comprising:
   generating, based upon the identified one or more subject sleep events, a notification describing the one or more sleep events; and
   transmitting the notification to the client device.

3. The method of claim 1, wherein receiving subject sound data comprises receiving the subject sound data from at least one audio sensor associated with the client device.

4. The method of claim 1, wherein receiving subject sound data comprises receiving the sound data from the client device positioned at a location within a threshold distance of the user during the sleep interval.

5. The method of claim 1 further comprising determining a duration of each identified subject sleep event.

6. The method of claim 1 further comprising:
determining that a first subject sleep event recurs during the sleep interval; and
determining a number of occurrences of the first subject sleep event.

7. The method of claim 1 further comprising:
determining a number of subject sleep events that occurred during the sleep interval; and
determining a level of sleep quality associated with the sleep interval based upon the number of subject sleep events.

8. The method of claim 1 further comprising:
identifying one or more subject sleep events occurring over a plurality of sleep intervals based upon respective subject sound data for each sleep interval of the plurality of sleep intervals;
identifying at least one sleep trend associated with the plurality of sleep intervals;
generating a notification describing the at least one sleep trend; and
transmitting the notification to the client device.

9. The method of claim 1 further comprising:
analyzing, using the machine learning algorithm, the sample sound data; and
identifying, based upon the analyzing, the plurality of sample characteristics.

10. A computer system for assessing sound to analyze a user's sleep, the computer system comprising:
a processor; and
a non-transitory, tangible, computer-readable storage medium having instructions stored thereon that, in response to execution by the processor, cause the processor to perform operations comprising:
storing sample sound data associated with a plurality of sample sleep events, the sample sound data including a plurality of sample characteristics each respectively associated with at least one sample sleep event of the plurality of sample sleep events;
receiving, from a client device, subject sound data collected during a sleep interval;
analyzing, using a machine learning algorithm, the subject sound data collected during the sleep interval;
identifying, based upon the analyzing, a subject characteristic associated with the subject sound data;
comparing the subject characteristic with the plurality of sample characteristics; and
determining, based upon the comparing, whether the subject characteristic substantially matches at least one sample characteristic to identify one or more subject sleep events occurring during the sleep interval.

11. The computer system of claim 10, wherein the processor is further configured to perform operations comprising:
generating, based upon the identified one or more subject sleep events, a notification describing the one or more sleep events; and
transmitting the notification to the client device.

12. The computer system of claim 10, wherein the processor is further configured to perform operations comprising receiving the subject sound data from at least one audio sensor associated with the client device.

13. The computer system of claim 10, wherein the processor is further configured to perform operations comprising receiving the sound data from the client device positioned at a location within a threshold distance of the user during the sleep interval.

14. The computer system of claim 10, wherein the processor is further configured to perform operations comprising determining a duration of each identified subject sleep event.

15. The computer system of claim 10, wherein the processor is further configured to perform operations comprising:
determining that a first subject sleep event recurs during the sleep interval; and
determining a number of occurrences of the first subject sleep event.

16. The computer system of claim 10, wherein the processor is further configured to perform operations comprising:
determining a number of subject sleep events that occurred during the sleep interval; and
determining a level of sleep quality associated with the sleep interval based upon the number of subject sleep events.

17. The computer system of claim 10, wherein the processor is further configured to perform operations comprising:
identifying one or more subject sleep events occurring over a plurality of sleep intervals based upon respective subject sound data for each sleep interval of the plurality of sleep intervals;
identifying at least one sleep trend associated with the plurality of sleep intervals;
generating a notification describing the at least one sleep trend; and
transmitting the notification to the client device.

18. A non-transitory computer readable medium that includes executable instructions for assessing sound to analyze a user's sleep, wherein when executed by a sound analysis computing device comprising at least one processor in communication with at least one memory device, the computer executable instructions cause the sound analysis computing device to:
store sample sound data associated with a plurality of sample sleep events, the sample sound data including a plurality of sample characteristics each respectively associated with at least one sample sleep event of the plurality of sample sleep events;
receive, from a client device, subject sound data collected during a sleep interval;
analyze, using a machine learning algorithm, the subject sound data collected during the sleep interval;
identify, based upon the analysis, a subject characteristic associated with the subject sound data;
compare the subject characteristic with the plurality of sample characteristics; and
determine, based upon the comparison, whether the subject characteristic substantially matches at least one sample characteristic to identify one or more subject sleep events occurring during the sleep interval.

19. The non-transitory computer readable medium of claim 18, wherein the computer executable instructions further cause the sound analysis computing device to:
determine a number of subject sleep events that occurred during the sleep interval; and
determine a level of sleep quality associated with the sleep interval based upon the number of subject sleep events.

20. The non-transitory computer readable medium of claim 18, wherein the computer executable instructions further cause the sound analysis computing device to:

identify one or more subject sleep events occurring over a plurality of sleep intervals based upon respective subject sound data for each sleep interval of the plurality of sleep intervals;

identify at least one sleep trend associated with the plurality of sleep intervals;

generate a notification describing the at least one sleep trend; and transmit the notification to the client device.

* * * * *